United States Patent
Ozai et al.

(10) Patent No.: US 9,796,817 B2
(45) Date of Patent: Oct. 24, 2017

(54) CURABLE COMPOSITION, SEMICONDUCTOR DEVICE, AND ESTER BOND-CONTAINING ORGANOSILICON COMPOUND

(71) Applicant: SHIN-ETSU CHEMICAL CO., LTD., Tokyo (JP)

(72) Inventors: Toshiyuki Ozai, Takasaki (JP); Masanari Moteki, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/108,708

(22) PCT Filed: Dec. 3, 2014

(86) PCT No.: PCT/JP2014/006041
§ 371 (c)(1),
(2) Date: Jun. 28, 2016

(87) PCT Pub. No.: WO2015/118594
PCT Pub. Date: Aug. 13, 2015

(65) Prior Publication Data
US 2016/0319078 A1    Nov. 3, 2016

(30) Foreign Application Priority Data
Feb. 7, 2014  (JP) .................. 2014-21871

(51) Int. Cl.
| | |
|---|---|
| H01L 29/66 | (2006.01) |
| C08G 77/14 | (2006.01) |
| C08G 77/60 | (2006.01) |
| C08K 5/54 | (2006.01) |
| C08G 77/12 | (2006.01) |
| C08G 77/20 | (2006.01) |
| H01L 33/56 | (2010.01) |
| C08G 77/52 | (2006.01) |
| C08G 77/50 | (2006.01) |
| C07F 7/08 | (2006.01) |
| C07F 7/21 | (2006.01) |
| C08K 5/5435 | (2006.01) |
| C08K 5/56 | (2006.01) |
| C08G 77/00 | (2006.01) |

(52) U.S. Cl.
CPC ............ *C08G 77/14* (2013.01); *C07F 7/0818* (2013.01); *C07F 7/21* (2013.01); *C08G 77/12* (2013.01); *C08G 77/20* (2013.01); *C08G 77/50* (2013.01); *C08G 77/52* (2013.01); *C08G 77/60* (2013.01); *C08G 77/80* (2013.01); *C08K 5/54* (2013.01); *C08K 5/5435* (2013.01); *C08K 5/56* (2013.01); *H01L 33/56* (2013.01)

(58) Field of Classification Search
CPC ........ C08G 77/14; C08G 77/12; C08G 77/20; C08G 77/50; C08G 77/52; C08G 77/60; C08G 77/80; C07F 7/21; C08K 5/54; C08K 5/5435; C08K 5/56; H01L 33/56
USPC ........................................... 257/100
See application file for complete search history.

(56) References Cited

FOREIGN PATENT DOCUMENTS

| | | |
|---|---|---|
| AU | 720234 B2 | 5/2000 |
| JP | S62-38453 A | 2/1987 |
| JP | H10-130391 A | 5/1998 |
| JP | H10-228249 A | 8/1998 |
| JP | H10-242513 A | 9/1998 |
| JP | H11-130865 A | 5/1999 |
| JP | 2000-123981 A | 4/2000 |
| JP | 2012-046604 A | 3/2012 |

OTHER PUBLICATIONS

Wang et al.; "Synthesis, Characterization and Degradation of Poly(silyl ester)s;" Macromolecules; Oct. 10, 1998; vol. 31, No. 22; pp. 7606-7612.
Weinberg et al; "Synthesis and Characterization of Degradable Poly(silyl ester)s;" Macromolecules; Jan. 13, 1998; vol. 31, No. 1; pp. 15-21.
Sommer et al; "Malonic Ester Syntheses with Organosilicon Compounds. New Silicon-containing Malonic Esters, Mono-and Dicarboxylic Acids, Barbituric Acids and a Disiloxanetetracarboxylic Acid;" J. Am. Chem. Soc.; Mar. 1954; vol. 76, No. 6; pp. 1609-1612.
Mar. 10, 2015 International Search Report issued in International Patent Application No. PCT/JP2014/006041.

*Primary Examiner* — Trung Q Dang
*Assistant Examiner* — Patricia Reddington
(74) *Attorney, Agent, or Firm* — Oliff PLC

(57) ABSTRACT

A curable composition including: (A) an ester bond-containing organosilicon compound having two or more addition reactive carbon-carbon double bonds in one molecule, shown by the following general formula (1); (B) a silicon compound having two or more silicon atom-bonded hydrogen atoms in one molecule; and (C) a hydrosilylation reaction catalyst. This provides a curable composition to give a cured product with low gas permeability as well as excellent crack resistance and light transmission property.

(1)

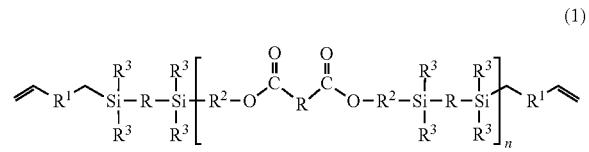

20 Claims, No Drawings

CURABLE COMPOSITION, SEMICONDUCTOR DEVICE, AND ESTER BOND-CONTAINING ORGANOSILICON COMPOUND

TECHNICAL FIELD

The present invention relates to a curable composition, a semiconductor device in which a semiconductor element is covered with the curable composition, and an ester bond-containing organosilicon compound suitably used for the curable composition.

BACKGROUND ART

Previously, epoxy resins have been generally used for optical devices or material for optical parts, particularly encapsulant for light emitting diode (LED) elements. Silicone resins also have been tried to use as molding material for LED elements (see Patent Document 1, Patent Document 2) or as material for color filters (see Patent Document 3), however, they are scarcely used practically.

Recently, due to attention paid to white LEDs, there arise problems about epoxy encapsulant such as yellowing by ultraviolet ray etc. and cracks caused by increasing calorific values due to miniaturization, which were not regarded as a problem previously and are pressing needs to be handled. As a countermeasure, it has been examined to use a cured product of a silicone resin having a large amount of phenyl groups in the molecule.

As the substrates for present LED use, however, silver substrates are mainly used. Silver is corroded by sulfur compounds in the air, which can lower the emission efficiency of LED in some cases. This phenomenon can be suppressed by cured product of the foregoing silicone resin having phenyl groups in a certain but less degree compared to conventional epoxy encapsulant.

As the countermeasure, it has been proposed a material which can compatible resistance to heat and corrosion of silver by using a curable composition having a polycyclic hydrocarbon group (see Patent Document 4). This composition, however, has a transition point as a resin near the room temperature, and accordingly has a problem to generate cracks due to temperature change to high temperature or low temperature.

CITATION LIST

Patent Literature

Patent Document 1: Japanese Unexamined Patent publication (Kokai) No. H10-228249
Patent Document 2: Japanese Unexamined Patent publication (Kokai) No. H10-242513
Patent Document 3: Japanese Unexamined Patent publication (Kokai) No. 2000-123981
Patent Document 4: Japanese Unexamined Patent publication (Kokai) No. 2012-46604

SUMMARY OF INVENTION

Technical Problem

The present invention was accomplished to solve the above-described problems. It is an object of the present invention to provide a curable composition to give a cured product with low gas permeability as well as excellent crack resistance and light transmission property.

It is another object of the present invention to provide a semiconductor device with good reliability in which a semiconductor element is covered with the inventive curable composition.

It is also an object of the present invention to provide an ester bond-containing organosilicon compound which can be suitably used for the inventive curable composition.

Solution to Problem

To solve the foregoing problems, the present invention provides a curable composition comprising:

(A) an ester bond-containing organosilicon compound having two or more addition reactive carbon-carbon double bonds in one molecule, shown by the following general formula (1),

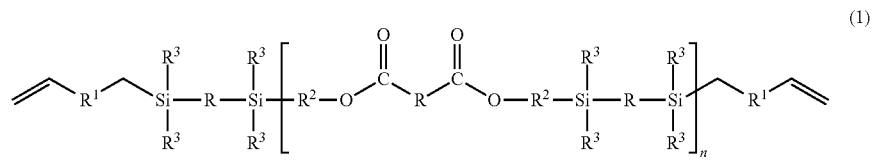

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10;

(B) a silicon compound having two or more silicon atom-bonded hydrogen atoms in one molecule; and (C) a hydrosilylation reaction catalyst.

Such a curable composition can be a curable composition to give a cured product with low gas permeability as well as good crack resistance and light transmission property.

The component (A) is preferably an addition reaction product of (a) an ester bond-containing organosilicon compound shown by the following general formula (2) and (b) an organic compound shown by the following general formula (3),

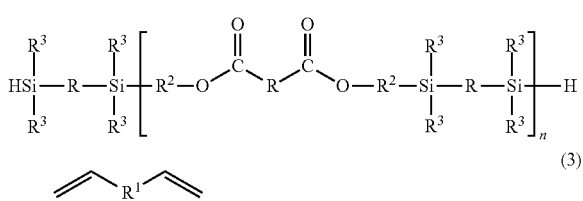
(2)

(3)

wherein "R", $R^1$, $R^2$, $R^3$, and "n" have the same meanings as defined above.

As described above, the component (A) can be easily obtained by an addition reaction of the component (a) and the component (b).

In this case, the component (a) is preferably an addition reaction product of (i) an ester bond-containing organic compound shown by the following general formula (4) and (ii) a silicon compound having two silicon atom-bonded hydrogen atoms in one molecule shown by the following general formula (5),

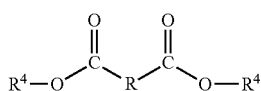
(4)

-continued

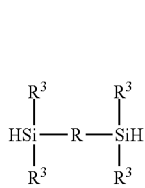
(5)

wherein "R" and $R^3$ have the same meanings as defined above, and $R^4$ independently represents a substituted or unsubstituted monovalent hydrocarbon group with 2 to 8 carbon atoms having an addition reactive carbon-carbon double bond.

As described above, the component (a) can be easily obtained by an addition reaction of the component (i) and the component (ii).

In this case, the component (a) is preferably a reaction product of the component (i) and the component (ii) in a molar ratio of (ii)/(i)=1.1 to 2.1.

By reacting in such a molar ratio, it is possible to effectively obtain the component (a), which has SiH groups at the both terminals of the molecular chain.

The "R" is preferably a substituted or unsubstituted divalent hydrocarbon group having 3 to 10 carbon atoms.

Particularly, the "R" is preferably either or both of a phenylene group and a divalent aliphatic hydrocarbon group having 3 to 10 carbon atoms.

Such an "R" brings the curable composition to give a cured product with lower gas permeability as well as better crack resistance and light transmission property.

The "n" is preferably an integer of 1 to 5.

Such an "n" brings the curable composition to give a cured product with lower gas permeability as well as better crack resistance and light transmission property.

Preferably, a refractive index of visible light at 25° C. of a cured product of the curable composition is 1.45 or more.

Such a refractive index is suitable for use as optical devices or material for optical parts.

Preferably, a light transmittance at 25° C. of a cured product of the curable composition is 80% or more.

Such a light transmittance is suitable for use as optical devices or material for optical parts.

The present invention also provides a semiconductor device in which a semiconductor element is covered with a cured product of the above curable composition.

Such a semiconductor device can be a reliable semiconductor device since it is covered with a cured product with low gas permeability as well as excellent crack resistance and light transmission property.

The present invention further provides an ester bond-containing organosilicon compound comprising two or more addition reactive carbon-carbon double bonds in one molecule, shown by the following general formula (1),

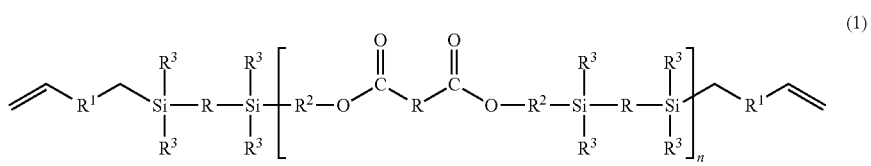
(1)

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10.

Such an ester bond-containing organosilicon compound can be suitably used for the foregoing curable composition of the present invention.

Advantageous Effects of Invention

As described above, the inventive curable composition can be a curable composition to give a cured product having low gas permeability, excellent crack resistance, a large refractive index of visible light, a high light transmittance even to a light in a short-wavelength region, excellent transparency, and high adhesive property to substrates.

Accordingly, the inventive curable composition can be suitably used for uses such as protection, encapsulating, adhesion, wavelength conversion, wavelength adjustment, or a lens for an LED element. It is also useful as various optical material such as lens material, encapsulant for an optical device or optical parts, and display material; insulator material for an electron device or electron parts; and coating material.

The inventive semiconductor device in which a semiconductor element is covered with a cured product of the inventive curable composition can be a reliable semiconductor device since it is covered with a cured product with low gas permeability as well as excellent crack resistance and light transmission property.

The inventive ester bond-containing organosilicon compound can be suitably used for the foregoing curable composition of the present invention.

DESCRIPTION OF EMBODIMENTS

As described above, it has been desired to develop an optical device material which can suppress corrosion of silver substrates and generation of cracks, particularly encapsulant for LED elements.

The present inventors have diligently studied to accomplish the foregoing problems and consequently found that the foregoing problems of corrosion of silver substrates and cracks can be improved by using a polymer having an ester bond in its main chain for optical device material, thereby brought the present invention to completion.

That is, the present invention is a curable composition comprising:

(A) an ester bond-containing organosilicon compound having two or more addition reactive carbon-carbon double bonds in one molecule, shown by the following general formula (1),

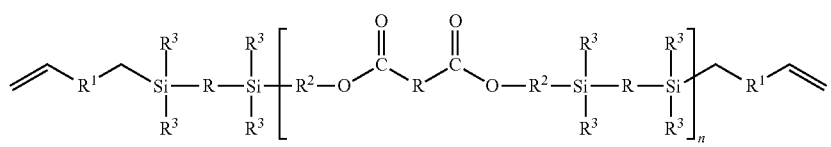

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10;

(B) a silicon compound having two or more silicon atom-bonded hydrogen atoms in one molecule; and (C) a hydrosilylation reaction catalyst.

Hereinafter, the present invention will be described in detail, but the present invention is not limited thereto.

The present invention provides an ester bond-containing organosilicon compound comprising two or more addition reactive carbon-carbon double bonds in one molecule, shown by the following general formula (1),

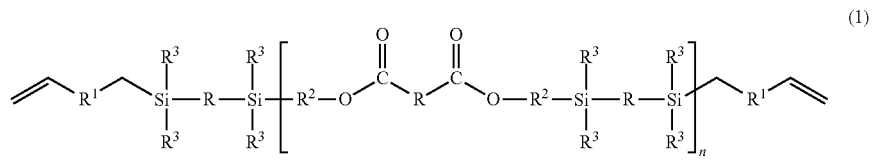

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10.

Such an ester bond-containing organosilicon compound can be suitably used as the component (A) of the inventive curable composition specified below.

Hereinafter, the inventive curable composition will be described in detail.

[Component (A)]

The component (A) is the foregoing inventive ester bond-containing organosilicon compound, that is an ester bond-containing organosilicon compound comprising two or more addition reactive carbon-carbon double bonds in one molecule, shown by the following general formula (1),

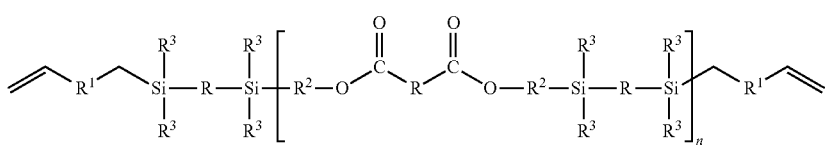

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10.

The number of the addition reactive carbon-carbon double bonds in the component (A) is two or more in one molecule. Particularly, the ones having the addition reactive carbon-carbon double bonds only at the both terminals of the molecule chain (i.e., having two addition reactive carbon-carbon double bonds) are preferable since that provides a cured product with good crack resistance and flexibility.

In the general formula (1), "R" independently represents a substituted or unsubstituted divalent hydrocarbon group having 1 to 12 carbon atoms, preferably a substituted or unsubstituted divalent hydrocarbon group having 3 to 10 carbon atoms, and more preferably either or both of a phenylene group and a divalent aliphatic hydrocarbon group having 3 to 10 carbon atoms.

Such an "R" is preferable since it provides a curable composition to give a cured product with lower gas permeability as well as better crack resistance and light transmission property.

In the general formula (1), $R^1$ independently represents a group selected from a substituted or unsubstituted divalent hydrocarbon group having 1 to 12 carbon atoms, a dimethylsilyl group, a methylphenylsilyl group, and a diphenylsilyl group; and preferably a dimethylsilyl group.

In the general formula (1), $R^2$ independently represents a substituted or unsubstituted divalent hydrocarbon group having 2 to 8 carbon atoms; and preferably a propylene group in view of easiness to procure the raw material.

In the general formula (1), $R^3$ independently represents a substituted or unsubstituted alkyl group having 1 to 8 carbon atoms; and preferably a methyl group in view of easiness to procure the raw material.

In the general formula (1), "n" is an integer of 1 to 10, preferably an integer of 1 to 5.

Such an "n" is preferable since it provides a curable composition to give a cured product with lower gas permeability as well as better crack resistance and light transmission property.

Such a component (A) can be easily obtained, for example, by an addition reaction of (a) an ester bond-containing organosilicon compound shown by the following general formula (2) and (b) an organic compound shown by the following general formula (3),

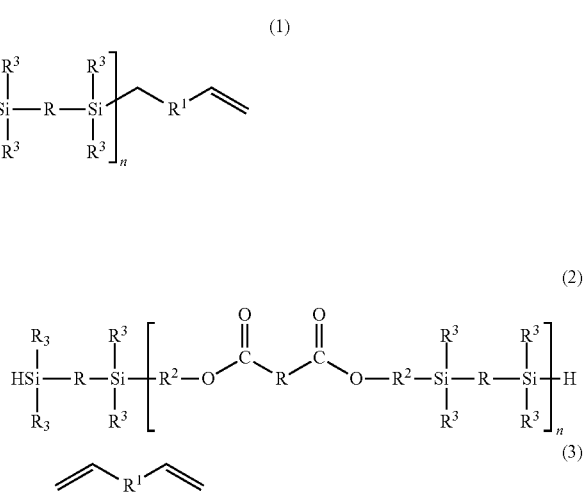

wherein "R", $R^1$, $R^2$, $R^3$, and "n" have the same meanings as defined above.

The component (a) can be easily obtained, for example, by an addition reaction of (1) an ester bond-containing organic compound shown by the following general formula (4) and (ii) a silicon compound having two silicon atom-bonded hydrogen atoms in one molecule shown by the following general formula (5),

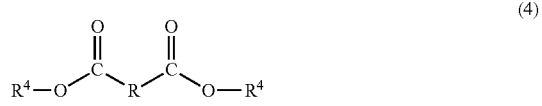

wherein "R" and $R^3$ have the same meanings as defined above, and $R^4$ independently represents a substituted or unsubstituted monovalent hydrocarbon group with 2 to 8 carbon atoms having an addition reactive carbon-carbon double bond.

In the general formula (4), $R^4$ independently represents a substituted or unsubstituted monovalent hydrocarbon group with 2 to 8 carbon atoms having an addition reactive carbon-carbon double bond; and preferably an allyl group in view of easiness to procure the raw material.

As the ester bond-containing organic compound shown by the general formula (4) of the component (i), specific examples shown by the following structural formulae are suitably used, but the component (i) is not limited thereto.

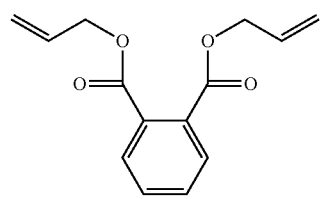

-continued

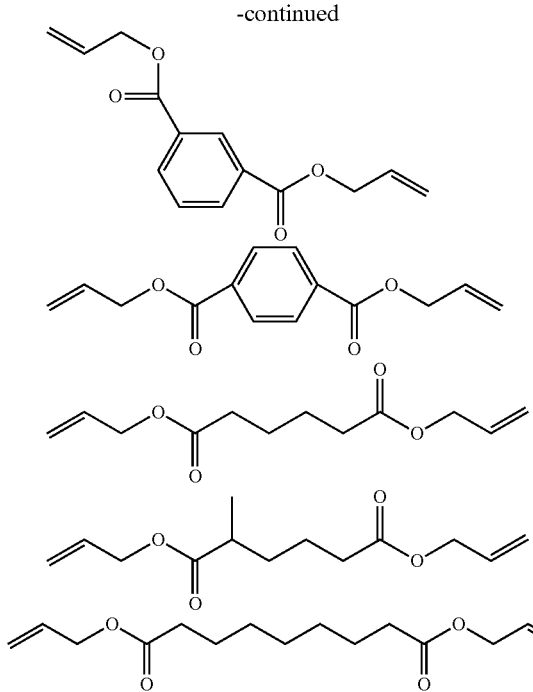

The component (i) may be used alone or in combination of two or more kinds.

As the silicon compound having two silicon atom-bonded hydrogen atoms in one molecule shown by the general formula (5) of the component (ii), specific examples shown by the following structural formulae are suitably used, but the component (ii) is not limited thereto.

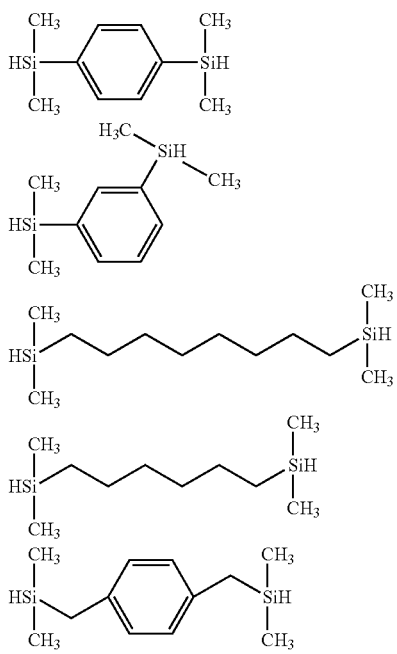

The component (ii) may be used alone or in combination of two or more kinds.

As the organic compound shown by the general formula (3) of the component (b), specific examples shown by the following structural formulae are suitably used, but the component (b) is not limited thereto.

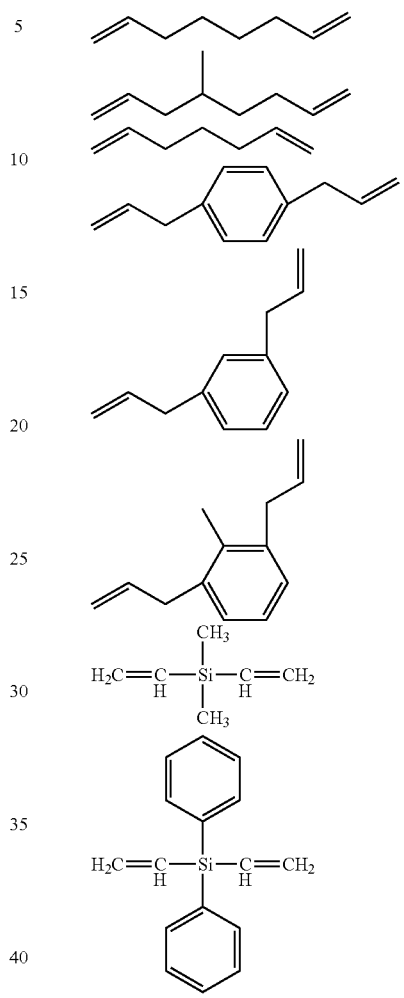

The component (b) may be used alone or in combination of two or more kinds.

<Synthesis of Component (A)>

The synthesis of the component (A) can be performed as follows, for example.

First, the component (i) having two addition reactive carbon-carbon double bonds and ester bonds in one molecule is mixed with the component (ii) having two SIR groups in such a way that the molar ratio (ii)/(i) is more than 1 and 10 or less, preferably more than 1 and 5 or less, more preferably 1.1 or more and 2.1 or less. They are subjected to an addition reaction under a presence of a hydrosilylation reaction catalyst to synthesize the component (a) having SiH groups at the both terminals of the molecular chain.

As described above, the component (a) having SiH groups derived from component (ii) at the both terminals of the molecular chain can be efficiently obtained by reacting the component (ii) in an excess amount by the molar ratio.

Then, thus synthesized component (a) is mixed with the component (b) having two addition reactive carbon-carbon double bonds in one molecule in such a way that the molar ratio (b)/(a) is more than 1 and 10 or less, preferably more than 1 and 5 or less. They are subjected to an addition reaction under a presence of a hydrosilylation reaction catalyst to synthesize the component (A) of the object.

As described above, the component (A) having addition reactive carbon-carbon double bonds derived from component (b) at the both terminals of the molecular chain can be efficiently obtained by reacting the component (b) in an excess amount by the molar ratio.

As the hydrosilylation reaction catalyst, previously known ones can be used.

Illustrative examples thereof include platinum-based catalysts such as metal platinum-supporting carbon powder, platinum black, platinum chloride, platinic chloride, reaction products of platinic chloride and monovalent alcohol, complexes of platinic chloride and olefin, platinum bis(acetoacetate); platinum group metal-based catalysts such as palladium-based catalysts and rhodium-based catalysts. The conditions of the addition reaction, use of a solvent(s), and so on are not particularly limited, and can be determined as usual.

The component (A) may be used alone or in combination of two or more kinds.

[Component (B)]

The component (B) is a silicon compound having two or more, preferably three or more silicon atom-bonded hydrogen atoms (SiH groups) in one molecule. This SiH group in the component (B) adds to an addition reactive carbon-carbon double bonds in the foregoing component (A) by hydrosilylation reaction to gives a cured product.

It is to be noted that the obtained structure of the cured product is preferably a three-dimensional network structure. Accordingly, the component (B) preferably has three or more SiH groups in one molecule.

Preferable examples of the component (B) include organohydrogenpolysiloxane with a viscosity at 25° C. of 1,000 mPa·s or less having two or more, favorably three or more SiH groups in one molecule represented by the following average composition formula (6), organohydrogensilane shown by the following general formula (7), and a combination thereof:

$$R'_x H_y SiO_{(4-x-y)/2} \quad (6)$$

$$R'_z SiH_{(4-z)} \quad (7)$$

wherein each R' may be the same or different and represents a substituted or unsubstituted monovalent hydrocarbon group; "x" and "y" are positive number satisfying $0.7 \leq x \leq 2.1$, $0.001 \leq y \leq 1.0$, and $0.8 \leq x+y \leq 2.6$, preferably $0.8 \leq x \leq 2$, $0.01 \leq y \leq 1$, $1 \leq x+y \leq 2.4$; and "z" is 1 or 2.

Each of the R's may be the same or different and represents a substituted or unsubstituted monovalent hydrocarbon group, preferably a monovalent hydrocarbon group having 1 to 12 carbon atoms. Particularly, a group which does not have an aliphatic unsaturated bond is preferable.

As such an R', a methyl group or a phenyl group is preferable.

Illustrative examples of the organohydrogensilane include $(CH_3)SiH_3$, $(CH_3)_2SiH_2$, $(C_6H_5)SiH_3$, etc. Illustrative examples of the organohydrogenpolysiloxane include 1,1,3,3-tetramethyldisiloxane, 1,3,5,7-tetra-methylcyclotetrasiloxane, methylhydrogenpolysiloxane the both terminals of which has been blocked with trimethylsiloxy groups, a dimethylsiloxane/methylhydrogensiloxane copolymer the both terminals of which has been blocked with trimethylsiloxy groups, dimethylpolysiloxane the both terminals of which has been blocked with dimethylhydrogensiloxy groups, a dimethylsiloxane/methylhydrogensiloxane copolymer the both terminals of which has been blocked with dimethylhydrogensiloxy groups, a methylhydrogensiloxane/diphenylsiloxane copolymer the both terminals of which has been blocked with trimethylsiloxy groups, a methylhydrogensiloxane/diphenyl-siloxane/dimethylsiloxane copolymer the both terminals of which has been blocked with trimethylsiloxy groups, a copolymer composed of a $(CH_3)_2HSiO_{1/2}$ unit and a $SiO_{4/2}$ unit; and a copolymer composed of a $(CH_3)_2HSiO_{1/2}$ unit, a $SiO_{4/2}$ unit, and a $(C_6H_5)SiO_{3/2}$ unit.

Although the molecular structure of the organohydrogenpolysiloxane can be any of a linear, a cyclic, a branched, and a three-dimensional network structure, the number of the silicon atom in one molecule (or degree of polymerization) is preferably about 3 to 1,000, particularly about 3 to 300.

Preferably, the viscosity of this organohydrogenpolysiloxane at 25° C. is 1,000 mPa·s or less, more preferably 0.1 to 500 mPa·s, further preferably 0.5 to 300 mPa·s.

It is to be noted that when the foregoing component (A) has a phenylene group, the organohydrogensilane or organohydrogenpolysiloxane of the component (B) preferably has a phenyl group also in view of ensuring the transparency and preventing separation during storage. In this case, phenyl groups preferably constitutes 5% by mol or more, more preferably 8 to 50% by mol, further preferably 10 to 30% by mol of all the groups bonded to silicon atoms (R's and hydrogen atoms) in the formula (6). It is also preferable to combine organohydrogenpolysiloxane in which phenyl groups constitutes less than 15% by mol, favorably 10% by mol or more and less than 15% by mol of all the groups bonded to silicon atoms (R's and hydrogen atoms) in the formula (6) with organohydrogenpolysiloxane in which phenyl groups constitutes 15% by mol or more, favorably 15% by mol or more and 50% by mol or less of all the groups bonded to silicon atoms (R's and hydrogen atoms) in the formula (6) in a mass ratio of 1:9 to 9:1, particularly 3:7 to 7:3.

The formulation amounts of the component (B) is preferably 2 to 100 parts by mass, particularly 10 to 100 parts by mass relative to 100 parts by mass of the component (A).

The component (B) can be added in an amount such that the molar ratio of addition reactive carbon-carbon double bonds in the component (A) and SiH groups in the component (B) (SiH groups/addition reactive carbon-carbon double bonds) is 0.5 to 5, preferably 0.8 to 4, more preferably 1 to 3.

As the component (B), it is also possible to use silicon compounds shown by the following structural formulae other than the foregoing organohydrogenpolysiloxane or organohydrogensilane,

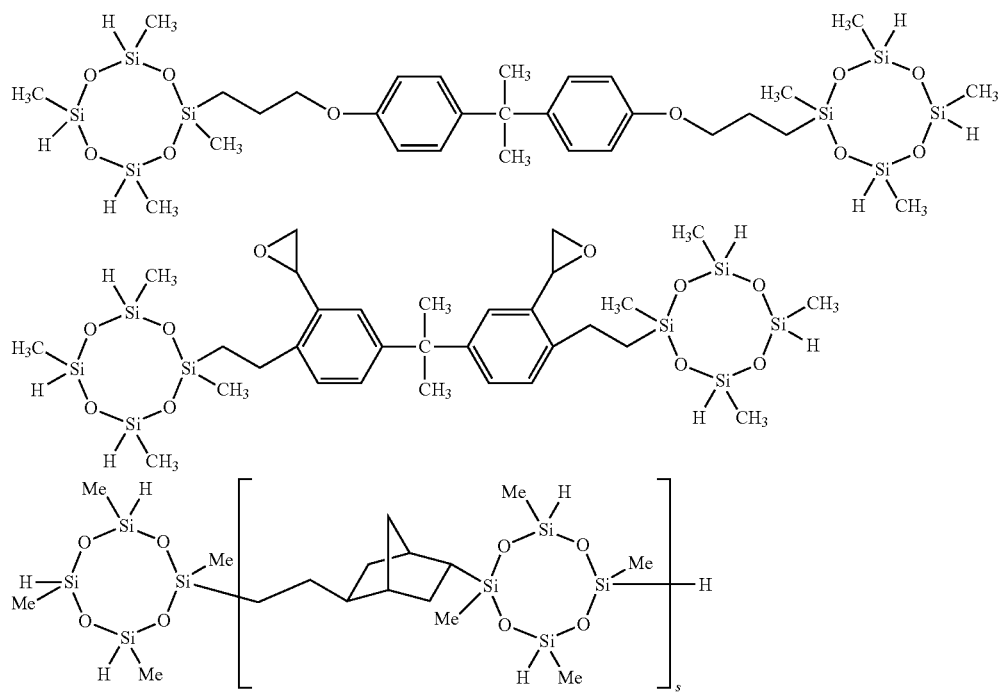

wherein Me represents a methyl group, and "s" is an integer of 1 to 100, preferably 1 to 10.

The component (B) may be used alone or in combination of two or more kinds.

[Component (C)]

The hydrosilylation reaction catalyst, which is the component (C) of the inventive curable composition, is the same as described in the synthesis of the component (A).

The formulation amount of the component (C) can be an effective amount as a catalyst, and is not particularly limited. However, it is preferable to formulate in such a way that the amount is approximately 1 to 500 ppm generally, particularly 2 to 100 ppm in terms of mass of the platinum group metal atom relative to the total mass of the components (A) and (B). Such formulation amount realizes a proper curing time required for the curing reaction and does not cause problems such as coloring of a cured product.

[Other Formulation Components]

The inventive curable composition can be formulated other components according to the needs in addition to the components (A) to (C).

<Antioxidant>

In a cured product of the inventive curable composition, the addition reactive carbon-carbon double band in the component (A) can remain unreacted in some cases. When the unreacted addition reactive carbon-carbon double bond is contained, the cured product can be oxidized by oxygen in the atmosphere to cause a risk of coloring.

Accordingly, the inventive curable composition can be formulated with antioxidant according to the needs to prevent the coloring beforehand.

Illustrative examples of the antioxidant include previously known ones such as 2,6-di-t-butyl-4-methyl-phenol, 2,5-di-t-amylhydroquinone, 2,5-di-t-butyl-hydroquinone, 4,4'-butylidenebis(3-methyl-6-t-butylphenol), 2,2'-methylenebis(4-methyl-6-t-butylphenol), and 2,2'-methylenebis(4-ethyl-6-t-butylphenol). These may be used alone or in combination of two or more kinds.

When using the antioxidant, the formulation amount can be an effective amount as an antioxidant, and is not particularly limited. However, the formulation amount is preferably about 10 to 10,000 ppm in general, particularly 100 to 1,000 ppm relative to the total mass of the components (A) and (B). Such formulation amount enables to exhibit a sufficient antioxidant ability to obtain a cured product with excellent optical property which does not occur coloring, cloudiness, and oxidative deterioration.

<Viscosity Modifier, Hardness Modifier>

It is possible to add inorganic filler such as nano-silica, fused silica, crystalline silica, titanium oxide, nano-alumina, alumina in order to adjust the viscosity of the inventive cured composition or the hardness of the cured product obtained from the composition, to enhance the strength of the cured product, or to improve the dispersity of a fluorescent substance when formulating it.

<Addition Reaction Controlling Agent>

In order to ensure the pot life, an addition reaction controlling agent such as 1-ethynylcyclohexanol and 3,5-dimethyl-1-hexyne-3-ol can be formulated.

<Light Stabilizer>

Furthermore, it is possible to use a light stabilizer in order to add resistance to photo-deterioration due to light energy such as sunbeam or fluorescent tube.

As this light stabilizer, a hindered amine based light stabilizer, which captures radicals generated by photo-oxidative deterioration, is preferable. The antioxidant effect is more improved by using it together with the foregoing antioxidant.

Illustrative examples of the light stabilizer include bis(2,2,6,6-tetramethyl-4-piperidil)sebacate, 4-benzoyl-2,2,6,6-tetramethylpiperidine.

<Others>

When using the inventive curable composition as an encapsulant, a silane coupling agent such as glycidoxypropyltrimethoxysilane can be added to improve the adhesion to a substrate, or a plasticizer can be added to prevent a crack.

The curing conditions of the inventive curable composition varies depending on its amount, and is not particularly limited. However, it is preferable to set the condition at 60 to 180° C. for 5 to 180 minutes in general.

Preferably, the refractive index of visible light (wavelength: 589 nm) at 25° C. of a cured product of the inventive curable composition is 1.45 or more. Such a refractive index is suitable for use in optical devices or material for optical parts.

Preferably, the light transmittance at 25° C. of a cured product of the inventive curable composition is 80% or more. Such a light transmittance is suitable for use in optical devices or material for optical parts.

Preferably, the gas permeability of a cured product of the inventive curable composition is 300 cc/m$^2$·day or less in view of suppressing corrosion of a silver substrate.

As described above, the inventive curable composition can be a curable composition to give a cured product having low gas permeability, excellent crack resistance, a large refractive index of visible light, a high light transmittance even to a light in a short-wavelength region, excellent transparency, and high adhesive property to substrates.

Accordingly, the inventive curable composition can be suitably used for uses such as protection, encapsulating, adhesion, wavelength conversion, wavelength adjustment or lens for an LED element. It is also useful as various optical material such as lens material, encapsulant for an optical device or optical parts, and display material; insulator material for an electron device or electron parts; and coating material.

The present invention further provides a semiconductor device in which a semiconductor element is covered with a cured product of the foregoing inventive curable composition.

Such a semiconductor device can be a reliable semiconductor device since it is covered with a cured product with low gas permeability as well as excellent crack resistance and light transmission property.

EXAMPLE

Hereinafter, the present invention will be specifically described with reference to Synthesis Examples, Examples and Comparative Examples, but the present invention is not limited thereto.

Synthesis Example 1

Synthesis of Component (A-1)

To a 500 mL four-neck flask equipped with a stirrer, a condenser, a dropping funnel, and a thermometer, 155.5 g (0.8 mol) of p-dimethylsilylbenzene and 50 g of toluene were added and heated to 85° C. with an oil bath. To this, 0.1 g of a platinum catalyst CAT-PL-50T (product of Shin-Etsu Chemical Co., Ltd.) was added, and 98.5 g (0.4 mol) of diallyl phthalate was added dropwise. After finishing the dropping, this was further stirred with heating at 85 to 95° C. for 5 hours, and concentrated at a time when 5 hours were passed to remove the solvent toluene and unreacted p-dimethyl-silylbenzene, thereby giving an intermediate shown by the following structural formula. After the removal, the intermediate was added dropwise to a 500 mL four-neck flask equipped with a stirrer, a condenser, a dropping funnel, and a thermometer, in which 65.6 g (0.8 mol) of hexadiene, 50 g of toluene, and 0.05 g of CAT-PL-50T had been previously introduced and heated to 85° C.

The structural formula of the intermediate is shown in the following,

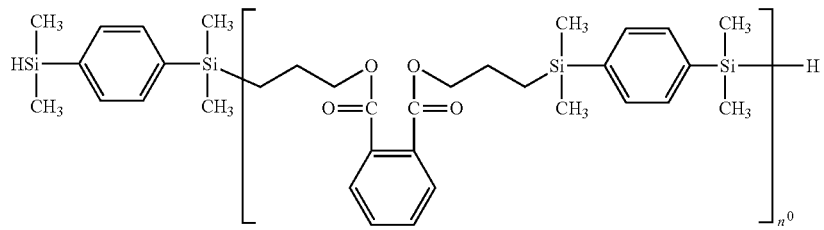

wherein $n^0$ is 1, 2, or 3.

After the finish of dropping the intermediate, the mixture was stirred at 85 to 95° C. for 5 hours. This was returned to room temperature after finishing the stirring, and then 3 g of activated charcoal was added and stirred for 1 hour. After the stirring, this was filtered and concentrated to give 232 g (yield: 81%) of the component (A-1).

The component (A-1) was analyzed by NMR, GPC, and so on to reveal that the component (A-1) was a mixture of (A-1-1), (A-1-2), and (A-1-3), in which $n^1$s in the following structural formula were 1, 2, and 3 respectively, and the molar ratio in the mixture was (A-1-1):(A-1-2):(A-1-3)≈4:3:2. The content of addition reactive carbon-carbon double bonds in the entire mixture was 0.17 mol/100 g.

The structural formula of the component (A-1) is shown in the following,

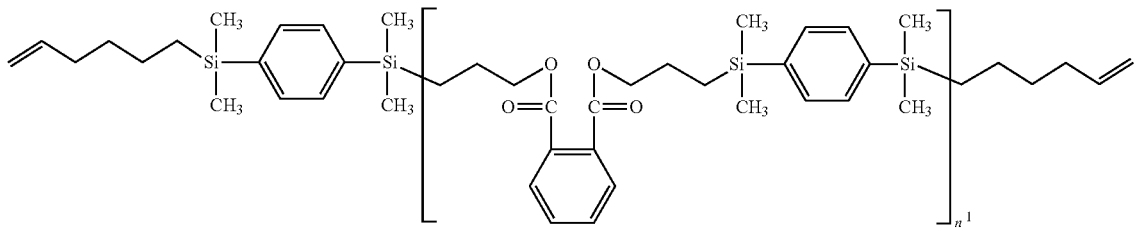

wherein $n^1$ is 1, 2, or 3.

Synthesis Example 2

Synthesis of Component (A-2)

Instead of hexadiene in Synthesis Example 1, 88.2 g (0.8 mol) of octadiene was used to give 261 g (yield: 76%) of component (A-2).

The component (A-2) was analyzed by NMR, GPC, and so on to reveal that the component (A-2) was a mixture of (A-2-1), (A-2-2), and (A-2-3), in which $n^2$s in the following structural formula were 1, 2, and 3 respectively, and the molar ratio in the mixture was (A-2-1):(A-2-2):(A-2-3)≈4:3:2. The content of addition reactive carbon-carbon double bonds in the entire mixture was 0.13 mol/100 g.

The structural formula of the component (A-2) is shown in the following,

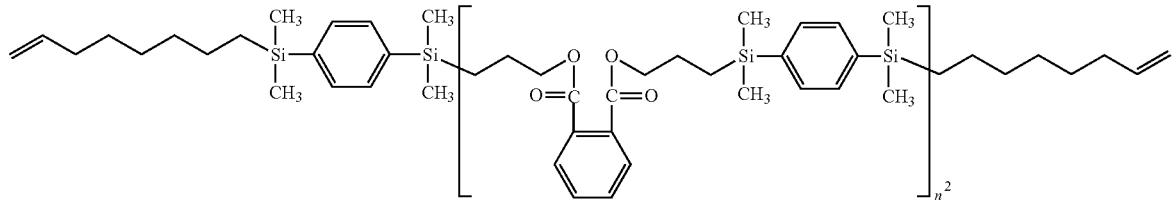

wherein $n^2$ is 1, 2, or 3.

Synthesis Example 3

Synthesis of Component (A-3)

Instead of hexadiene in Synthesis Example 1, 89.84 g (0.8 mol) of dimethyldivinylsilane was used to give 283 g (yield: 82%) of component (A-3).

The component (A-3) was analyzed by NMR, GPC, and so on to reveal that the component (A-3) was a mixture of (A-3-1), (A-3-2), and (A-3-3), in which $n^3$s in the following structural formula were 1, 2, and 3 respectively, and the molar ratio in the mixture was (A-3-1):(A-3-2):(A-3-3)≈4:3:1. The content of addition reactive carbon-carbon double bonds in the entire mixture was 0.19 mol/100 g.

The structural formula of the component (A-3) is shown in the following,

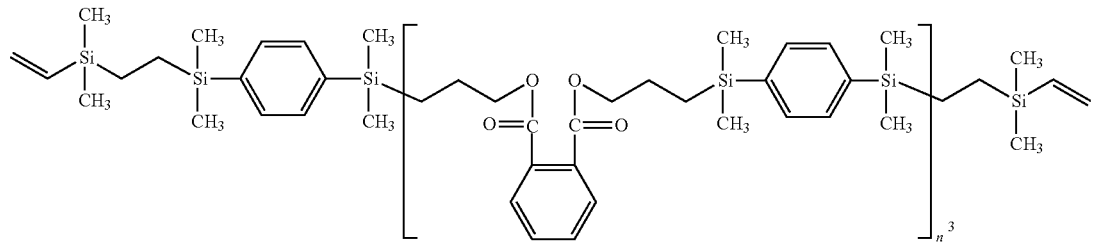

wherein $n^3$ is 1, 2, or 3.

Example 1

To 100 parts by mass of the component (A-1) synthesized in Synthesis Example 1, 25 parts by mass of phenylmethylhydrogensiloxane with a viscosity of 10 mPa·s and a hydrogen gas yield of 150 ml/g having 30% by mol of phenyl groups relative to the total amount of silicon atom-bonded methyl groups, phenyl groups, and hydrogen atoms (SiH groups); 0.2 parts by mass of ethynylcyclohexanol as a reaction controlling agent, and 1 part by mass of glycidoxypropyltrimethoxysilane as a silane coupling agent were added. To this mixture, a platinum catalyst was added in an amount of 20 ppm in terms of mass of the platinum atom, followed by homogeneous mixing to give a curable composition.

Example 2

The same procedure as in Example 1 was carried out except that 100 parts by mass of the component (A-2) synthesized in Synthesis Example 2 was used instead of 100 parts by mass of the component (A-1) in Example 1 to give a cured composition.

Example 3

The same procedure as in Example 1 was carried out except that 100 parts by mass of the component (A-3) synthesized in Synthesis Example 3 was used instead of 100 parts by mass of the component (A-1) in Example 1 to give a cured composition.

Comparative Example 1

A hydrolysis reaction was carried out at 50 to 60° C. for 5 hours by introducing 300 g of toluene and 300 g of water, followed by dropping 109 g (0.55 mol) of phenyltrimethoxysilane, 35 g (0.25 mol) of vinylmethyl-dichlorosilane, and 25.8 g (0.2 mol) of dimethyl-dichlorosilane. After the reaction was finished, washing was carried out by water until the water layer changed to neutral to prepare 190 g of 50% by mass toluene solution of organopolysiloxane copolymer (silicone resin) having an average composition of $(CH_3)_{0.65}(C_6H_5)_{0.55}(CH_2=CH)_{0.25}SiO_{1.28}$ composed of $(C_6H_5)SiO_{3/2}$ unit, $(CH_2=CH)(CH_3)SiO_{2/2}$ unit, and $(CH_3)_2SiO_{2/2}$ unit.

To 100 parts by mass of this resin solution, 15 parts by mass of phenylmethylsiloxane with a viscosity of 700 mPa·s and a refractive index of 1.51, the both terminals of which has been blocked with vinyldimethyl-silyl groups, and having 30% by mol of phenyl groups relative to the total amount of silicon atom-bonded methyl groups, phenyl groups, and vinyl groups; and 15 parts by mass of phenylmethylhydrogensiloxane with a viscosity of 10 mPa·s and an amount of hydrogen gas generated of 150 ml/g having 30% by mol of phenyl groups relative to the total amount of silicon atom-bonded methyl groups, phenyl groups, and hydrogen atoms (SiH groups) were added and mixed, followed by stripping at 150° C. under reduced pressure till the distillate disappeared. This was cooled to room temperature, and then 0.2 parts by mass of ethynylcyclohexanol as a reaction controlling agent and 1 part by mass of glycidoxypropyltrimethoxysilane were added. To this mixture, a platinum catalyst was added in an amount of 20 ppm in terms of mass of the platinum atom, followed by homogeneous mixing to give a curable composition.

Comparative Example 2

A hydrolysis reaction was carried out at 50 to 60° C. for 5 hours by introducing 500 g of toluene and 500 g of water, followed by dropping 116 g (0.55 mol) of phenyltrichlorosilane, 35 g (0.25 mol) of vinylmethyl-dichlorosilane, and 26 g (0.2 mol) of dimethyldichloro-silane. After the reaction was finished, washing was carried out by water until the water layer changed to neutral to prepare 50% by mass toluene solution of organopolysiloxane resin copolymer (silicone resin) represented by an average composition of $(CH_3)_{0.65}(C_6H_5)_{0.55}(CH_2=CH)_{0.25}SiO_{1.28}$ composed of $(C_6H_5)SiO_{3/2}$ unit, $(CH_2=CH)(CH_3)SiO_{2/2}$ unit, and $(CH_3)_2 SiO_{2/2}$ unit.

To 100 parts by mass of this resin solution, 10 parts by mass of phenylmethylhydrogensiloxane with a viscosity of 10 mPa·s and an amount of hydrogen gas generated of 150 ml/g having 20% by mol of phenyl groups relative to the total amount of silicon atom-bonded methyl groups, phenyl groups, and hydrogen atoms (SiH groups) were added and mixed, followed by stripping at 150° C. under reduced pressure till the distillate disappeared. This was cooled to room temperature, and then 0.2 parts by mass of ethynylcyclohexanol as a reaction controlling agent and 1 part by mass of glycidoxypropyltrimethoxysilane were added. To this mixture, a platinum catalyst was added in an amount of 20 ppm in terms of mass of the platinum atom, followed by homogeneous mixing to give a curable composition.

<Performance Evaluation Method>

On the cured products of curable compositions obtained in the foregoing Examples and Comparative Examples, the properties were evaluated in accordance with the following methods.

[Hardness]

Each composition was subjected to stirring, mixing, and defoaming, and then casted into a mold made of assembled glass plates so as to form a thickness of 2 mm. This was heated at 120° C. for 30 minutes to be cured, and post cured in a 150° C. drier for 3 hours to make a sample. By following ASTM D 2240, hardness (Shore D) of each sample was measured. The measured results are shown in Table 1.

[Refractive Index]

On the samples of each cured product used in the hardness test, a refractive index of light with an wavelength of 589 nm at 25° C. was measured by using a digital refractometer RX-5000 produced by ATAGO CO., LTD. The measured results are shown in Table 1.

[Light Transmittance]

On the samples of each cured product used in the hardness test, a transmittance of light with an wavelength of 400 nm at 25° C. was measured by using a spectrophotometer. The measured results are shown in Table 1.

[Crack Resistance (Durability)]

Each composition casted into a chip-type LED circuit was exposed at 260° C. for 3 minutes, and the cured product part covering each LED circuit was checked whether a crack exist or not. Furthermore, an LED circuit encapsulated with a cured product of each composition was put into a thermal shock tester which runs at −40° C. for 30 minutes and at 120° C. for 30 minutes for each cycle, and the cured product part on each LED circuit after 500 times of the cycle was checked whether a crack exist or not. The measured results are shown in Table 1.

[Oxygen Gas Permeability]

Each composition was subjected to stirring, mixing, and defoaming, and then casted into a mold made of assembled glass plates so as to form a thickness of 1 mm. This was heated at 120° C. for 30 minutes to be cured, and post cured in a 150° C. drier for 3 hours to make a sample. With Model 8000 produced by Illinois Instruments, Inc., gas permeability of each cured product was measured by an equal-pressure method. The measured results are shown in Table 1.

TABLE 1

| Items | Example 1 | Example 2 | Example 3 | Comparative Example 1 | Comparative Example 2 |
|---|---|---|---|---|---|
| Hardness (Shore-D) | 35 | 30 | 40 | 40 | 55 |
| Refractive index | 1.53 | 1.53 | 1.49 | 1.52 | 1.52 |
| Light transmittance (%) | 89 | 89 | 90 | 88 | 89 |
| Crack after 260° C. × 3 min. | none | none | none | none | exist |
| Crack after 500 cycles | none | none | none | exist | exist |
| Oxygen gas permeability (cc/m² · day) | 250 | 300 | 230 | 1000 | 800 |

As shown in Table 1, each of the cured products of Examples 1 to 3, comprising respective ester bond-containing organosilicon compounds, which are the component (A) of the inventive curable composition, showed an excellent light transmittance and low oxygen gas permeability, and did not generate a crack in the durability test.

On the other hand, each of the cured products of Comparative Example 1 and Comparative Example 2, which did not contain the component (A) of the inventive curable composition, generated a crack in the durability test and showed high oxygen gas permeability.

As described above, it has revealed that the inventive curable composition has low gas permeability and an excellent light transmission property, and can suppress the generation of a crack due to temperature change. Moreover, it has suggested that corrosion of a silver substrate can be suppressed because of the low gas permeability.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A curable composition comprising:
   (A) an ester bond-containing organosilicon compound having two or more addition reactive carbon-carbon double bonds in one molecule, shown by the following general formula (1),

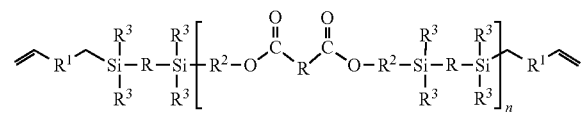

(1)

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10;
   (B) a silicon compound having two or more silicon atom-bonded hydrogen atoms in one molecule; and
   (C) a hydrosilylation reaction catalyst.

2. The curable composition according to claim 1, wherein the component (A) is an addition reaction product of (a) an ester bond-containing organosilicon compound shown by the following general formula (2) and (b) an organic compound shown by the following general formula (3),

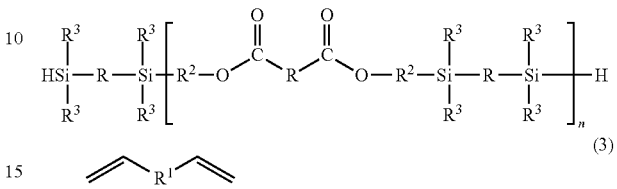

(2)

(3)

wherein "R", $R^1$, $R^2$, $R^3$, and "n" have the same meanings as defined above.

3. The curable composition according to claim 2, wherein the component (a) is an addition reaction product of (i) an ester bond-containing organic compound shown by the following general formula (4) and (ii) a silicon compound having two silicon atom-bonded hydrogen atoms in one molecule shown by the following general formula (5),

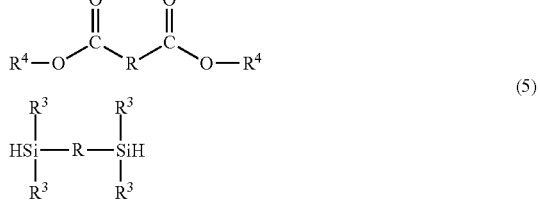

(4)

(5)

wherein "R" and $R^3$ have the same meanings as defined above, and $R^4$ independently represents a substituted or unsubstituted monovalent hydrocarbon group with 2 to 8 carbon atoms having an addition reactive carbon-carbon double bond.

4. The curable composition according to claim 3, wherein the component (a) is a reaction product of the component (i) and the component (ii) in a molar ratio of (ii)/(i)=1.1 to 2.1.

5. The curable composition according to claim 1, wherein the "R" represents a substituted or unsubstituted divalent hydrocarbon group having 3 to 10 carbon atoms.

6. The curable composition according to claim 2, wherein the "R" represents a substituted or unsubstituted divalent hydrocarbon group having 3 to 10 carbon atoms.

7. The curable composition according to claim 3, wherein the "R" represents a substituted or unsubstituted divalent hydrocarbon group having 3 to 10 carbon atoms.

8. The curable composition according to claim 4, wherein the "R" represents a substituted or unsubstituted divalent hydrocarbon group having 3 to 10 carbon atoms.

9. The curable composition according to claim 5, wherein the "R" represents either or both of a phenylene group and a divalent aliphatic hydrocarbon group having 3 to 10 carbon atoms.

10. The curable composition according to claim 6, wherein the "R" represents either or both of a phenylene group and a divalent aliphatic hydrocarbon group having 3 to 10 carbon atoms.

11. The curable composition according to claim 7, wherein the "R" represents either or both of a phenylene group and a divalent aliphatic hydrocarbon group having 3 to 10 carbon atoms.

12. The curable composition according to claim 8, wherein the "R" represents either or both of a phenylene group and a divalent aliphatic hydrocarbon group having 3 to 10 carbon atoms.

13. The curable composition according to claim 1, wherein the "n" is an integer of 1 to 5.

14. The curable composition according to claim 2, wherein the "n" is an integer of 1 to 5.

15. The curable composition according to claim 1, wherein a refractive index of visible light at 25° C. of a cured product of the curable composition is 1.45 or more.

16. The curable composition according to claim 1, wherein a light transmittance at 25° C. of a cured product of the curable composition is 80% or more.

17. A semiconductor device, wherein a semiconductor element is covered with a cured product of the curable composition according to claim 1.

18. A semiconductor device, wherein a semiconductor element is covered with a cured product of the curable composition according to claim 2.

19. A semiconductor device, wherein a semiconductor element is covered with a cured product of the curable composition according to claim 3.

20. An ester bond-containing organosilicon compound comprising two or more addition reactive carbon-carbon double bonds in one molecule, shown by the following general formula (1),

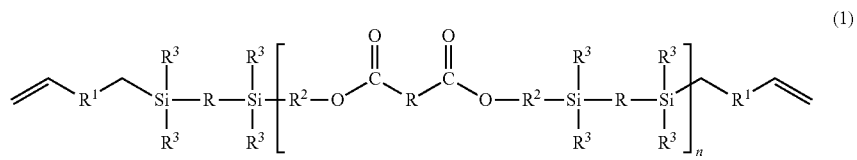

(1)

wherein "R" independently represents a substituted or unsubstituted divalent hydrocarbon group having 1 to 12 carbon atoms; $R^1$ independently represents a group selected from a substituted or unsubstituted divalent hydrocarbon group having 1 to 12 carbon atoms, a dimethylsilyl group, a methylphenylsilyl group, and a diphenylsilyl group; $R^2$ independently represents a substituted or unsubstituted divalent hydrocarbon group having 2 to 8 carbon atoms; $R^3$ independently represents a substituted or unsubstituted alkyl group having 1 to 8 carbon atoms; and "n" is an integer of 1 to 10.

* * * * *